United States Patent [19]

Kamishita

[11] Patent Number: 4,472,376

[45] Date of Patent: Sep. 18, 1984

[54] PHARMACEUTICAL INSERTION COMPOSITIONS AND A PROCESS FOR PRODUCING THE SAME

[75] Inventor: Takuzo Kamishita, Takatsuki, Japan

[73] Assignee: Toko Yakuhin Kogyo Kabushiki Kaisha, Osaka, Japan

[21] Appl. No.: 462,375

[22] Filed: Jan. 31, 1983

Related U.S. Application Data

[60] Continuation of Ser. No. 36,492, May 7, 1979, abandoned, which is a division of Ser. No. 802,960, Jun. 2, 1977, abandoned.

[30] Foreign Application Priority Data

Jun. 21, 1976 [JP] Japan ................................. 51-72960

[51] Int. Cl.$^3$ ..................... A61K 31/19; A61K 31/78; A61K 37/26
[52] U.S. Cl. ..................................... 424/81; 424/178; 424/317
[58] Field of Search .......................... 424/81, 178, 317

[56] References Cited

U.S. PATENT DOCUMENTS 3,749,773  7/1973  Ninger et al. .......................... 424/81

Primary Examiner—Staniey I. Priedman
Attorney, Agent, or Firm—Armstrong, Nikaido, Marmelstein & Kubovcik

[57] ABSTRACT

A phamaceutical insertion composition comprising a mixture of an aqueous solution of carboxyvinyl polymer with a water-soluble basic compound and a pharmaceutical ingredient, said mixture being a gel having a pH value of from 4 to 10 and a viscosity of from 5,000 to 100,000 centipoises at 20° C., which composition is applied to the rectal, vaginal or urethral tissue and the pharmaceutical ingredient is absorbed into the blood stream of the human body.

3 Claims, No Drawings

PHARMACEUTICAL INSERTION COMPOSITIONS AND A PROCESS FOR PRODUCING THE SAME

This is a continuation of application Ser. No. 36,492, filed May 7, 1979, which, in turn, is a division of application Ser. No. 802,960, filed June 2, 1977, both are now abandoned.

BACKGROUND OF THE INVENTION

In the past pharmaceutical composition of a similar kind have been used in the form of solid suppositories having an oil or fat base, or as liquid agents. However, liquid agents are apt to flow out or be excreted from the body after insertion and the pharmaceutical ingredient is not sufficiently absorbed in the body. A suppository is a pharmaceutical composition which is solid at room temperature, wherein a pharmaceutical ingredient is contained in a base composition, such as cacao butter, which melts gradually under body heat. Such a composition requires a long time for melting in the body, during which time a film of the base composition is formed on the mucous membrane of the body, and the absorption of the pharmaceutical ingredient into the body is suppressed, thus curtailing the medicinal effect. A suppository must be kept at low temperatures so as to preserve a fixed shape and maintain a sufficient solidity when inserted into the body. Also, a suppository gives an uncomfortable feeling to the patient at the time of insertion, it is difficult to insert, and when inserted into the rectum it maybe excreted in the original state. Thus, the suppository has been not only inconvenient in its use but also insufficient in its medicinal effect.

On the other hand, pharmaceutical compositions having been commonly administered by injecting into the body. Injection is an effective method for providing a desired concentration in the blood and realizing a medicinal effect, but it may give rise to a nerve disturbance, especially contraction of muscle tissue such as a contraction of quadriceps femoria muscle. For this reason, administration by injection has come to be strictly restricted.

In an attempt to obtain a pharmaceutical composition which can provide sufficient medicinal effect and can be administered safely in suitable dosages, the present inventor conducted strenous study and found that a pharmaceutical composition, comprising a gel form base composition having a specific viscosity based on a carboxyvinyl polymer impregnated with a pharmaceutical ingredient, has excellent properties when compared with the conventional suppositories and fully satisfies its intended medicinal purpose.

SUMMARY OF THE INVENTION

The present invention relates to a novel pharmaceutical composition, more particularly, to a pharmaceutical composition in gel form suitable for insertion into the rectum, vagina and urethra, which composition comprises a mixture of an aqueous solution of carboxyvinyl polymer with a water-soluble basic compound and a pharmaceutical ingredient, said mixture being a gel having a pH value of from 4 to 10 and a viscosity of from 5,000 to 100,000 centipoises at 20° C.

DETAILED DESCRIPTION OF THE INVENTION

According to the present invention, there is provided a process for preparation of a pharmaceutical insertion composition which process comprises mixing uniformly into an aqueous solution of carboxyvinyl polymer, a water-soluble basic compound and a pharmaceutical ingredient to form a gel composition having a viscosity in a range of from 5,000 to 100,000 centipoises at 20° C. The resulting composition is suitable for insertion into the rectum, vagina or urethra. The base compound for the composition comprises a mixture of an aqueous solution of carboxyvinyl polymer with a water-soluble basic compound, said mixture having a pH value of from 6.5 to 7.5 and a viscosity of from 5,000 to 100,000 centipoises at 20° C. And a pharmaceutical insertion composition suitable for insertion into rectum, vagina, or urethra, comprises a mixture of an aqueous solution of carboxyvinyl polymer with a water-soluble basic compound and pharmaceutical ingredient, said mixture being a gel having a pH value of from 4 to 10 and a viscosity of from 5,000 to 100,000 centipoises at 20° C.

The carboxyvinyl polymer that may be employed in accordance with the present invention is vinyl polymer with active carboxyl groups white powder, highly ionic and slightly acidic, and hydrophylic polymer which can be prepared by polymerising a monomer mixture consisting mainly of acrylic acid, as shown in Chem. Eng. News 36, No. 39, p.64 (Sept. 29, 1958). Carbopol 934, 940 and 941, which are available commercially from the Goodrich Chemical Co., can also be used in the present invention. The carboxyvinyl polymer has free carboxyl groups, and is acidic in aqueous solution. When it is neutralized with a basic compound, it becomes a viscous gel.

In the present invention, the water-soluble basic compounds to be used for neutralizing the carboxyvinyl polymer are suitably, for example, the following amines: lower-alkylamines (e.g., methylamine, ethylamine, propylamine), di-lower-alkylamines (e.g., dimethylamine, diethylamine, dipropylamine), tri-lower-alkylamines (e.g., trimethylamine, triethylamine, tripropylamine), lower-alkanolamines (e.g., methanolamine, ethanolamine, propanolamine, etc.), di-lower-alkanolamines (e.g., diethanolamine, dimethanolamine, dipropanolamine, dibutanolamine, etc.), tri-lower-alkanolamines (e.g., trimethanolamine, triethanolamine, tripropanolamine, tributanolamine, etc.) and trimethylolaminomethane. The term lower alkyl or lower alkanol refers to compounds having an alkyl chain of up to 6 carbon atoms. In addition to the above amines, inorganic bases such as aqueous solution of ammonia and alkali metal hydroxide, etc. may be used. Regardless of the type of water-soluble basic compound used, neutralization of the carboxyvinyl polymer will provide a gel almost same the viscosity.

The neutralization of the carboxyvinyl polymer by the water-soluble basic compound is suitably conducted in such a manner that generally a gel composition of the proper viscosity is formed at a substantially neutral pH, i.e., a pH value of from 6 to 8. Depending upon the pharmaceutical ingredient, a liquid form in which the ingredient has the most suitable stability is adopted. Upon adding the pharmaceutical ingredient, the pH of the gel form composition in the present invention may vary within the range of from 4 to 10.

In the present invention, the pharmaceutical ingredient usable may be either water-soluble or insoluble in water. When a pharmaceutical ingredient which is insoluble in water is used, the resulting gel composition become turbid, but does not settle in the composition, so that there is no trouble in dosage. However, it is preferred to use a solubilizer to make the composition transparent or to accelerate absorption in the body or to dissolve the pharmaceutical composition previously in a water-soluble organic solvent. Such water-soluble organic solvents include propylene glycol, polyethylene glycol the molecular weight of which is between 300 and 400, crotamiton, lauryl diethanolamide, etc. Among the above, propylene glycol is most suitable because of its great universality in use. A water-soluble basic compound may also function as a solvent. As solubilizing agents, there may be exemplified nonionic surface active agents, such as polyoxyethylene sorbitan fatty acid ester (e.g., polyoxyethylene sorbitan monopalmitate, polyoxyethylene sorbitan monostearate), polyoxyethylene alkyl ether (e.g., polyoxyethylene lauryl ether, polyoxyethylene cetyl ether, polyoxyethylene stearyl ether, polyoxyethylene oleyl ether, polyoxyethylene behenyl ether), and benzyl alcohol etc.

The pharmaceutical ingredient to be used for the present invention is preferably one stable in the composition, i.e., in the aqueous medium and in the nonionic surface active agent. Suitable pharmaceutical ingredients to be used in the composition of the present invention are, for example, antipyretic, anti-inflammatory and analgesic (e.g., aminopyrine, sulpyrine, ethyl aminobezoate, benzyl alcohol, indomethacin, ibuprofen, ibufenac, flufenamic acid, ketoprofen, flurbiprofen, phenylbutazone, oxyfenbutazone, dichlofenac sodium, mepirizole), adrenal cortical hormones and derivatives thereof (e.g., prednisolone, cortisone, triameinolone, betamethasone, hydrocortisone, dexamethasone, methyl prednisolone, fluocinolone, dexamethasone acetate, triamcinolone acetonide, fluocinolone acetonide, dexamethasone valerate, betamethasone valerate, betamethazone bensoate, flumethasone, prednisolone acetate, dexamethasone acetate, hydrocortisone valerate, dexamethasone valerate), anti-cancer and anti-tumor agents (e.g., 5-fluorouracil and its derivatives), antibiotics (e.g., chloramphenicol, tetracycline, penicillin, cephalosporin and their derivatives), antituberculosis agent (e.g., isoniazid, streptomycin), hormon agents (e.g., estradiol, teststerone), hypotensers (e.g., reserpine), various sulfamines, lowering agents of blood sugar level (e.g., insuline) and other germicidal and anticeptics. As such, extensive applications are possible.

In the process of the present invention, a pharmaceutical ingredient is dissolved or dispersed in an aqueous solution of carboxyvinyl polymer, uniformly mixed by stirring during the addition of the water-soluble basic compound, and the pH is adjusted to 4 to 10. Alternatively the water-soluble basic compound is mixed while stirring with an aqueous solution of carboxyvinyl polymer to form a gel, to which the pharmaceutical ingredient is added to form a gel composition. The resulting gel composition has a viscosity in the range of from 5,000 to 100,000 centipoises at 20° C. When the viscosity of the gel is lower than 5,000 centipoises, the composition has a strong fluidity and is liable to flow out from the body, providing an undesirable state, when the viscosity is above 100,000 centipoises, the composition becomes too hard and causes difficulty during insertion. The compositions having a viscosity of from 10,000 to 60,000 centipoises are generally most desirable in the present invention. At a low viscosity, the pharmaceutical ingredient is quickly absorbed into the body, but as the viscosity increases a longer time is required for the collapse of the gel, thereby providing a slow absorption of the pharmaceutical ingredient into the body to preserve the medicinal effect. Accordingly, for attaining a quick absorption into the body, and for use as a germicidal or antiseptic, a gel having a relatively low viscosity is preferred. For carrying a pharmaceutical ingredient which is to be maintained at the effective concentration in the blood for a long duration, a gel having relatively high viscosity is suitably used. The viscosity is affected to some extent by the pharmaceutical ingredient to be added, mainly by the concentration of the carboxyvinyl polymer. In order to obtain a gel form composition of a desired viscosity, the carboxyvinyl polymer is used in aqueous solution in an amount ranging from 0.1 to 5.0% by weight of the final gel composition. In case the viscosity is drastically lowered because of nature of the pharmaceutical ingredient to be added, the ingredient may be formed into a gel having a desired viscosity by the use of an aqueous solution having a higher carboxyvinyl polymer content.

The gel form pharmaceutical insertion composition of the present invention is inserted into the rectum, vagina and urethra by means of an insertion instrument. When the pharmaceutical composition is inserted, the gel thereof favorably adheres to the mucous membrane, collapses, and is liquified, by which means the pharmaceutical ingredient is absorbed into the body. Especially, when the pharmaceutical composition is inserted into the rectum, the pharmaceutical ingredient is favorably absorbed from the mucous membrane of rectum, transferred into blood and carried to the affected part at a high concentration to provide the curing effect. On the other hand, the carboxyvinyl polymer and the water-soluble basic compound which neutralizes the carboxyvinyl polymer are not absorbed into the body and they are entirely harmless. The pharmaceutical insertion composition of the present invention gives no stimulus to the mucous membrane.

From the practical point of view it is generally suitable for the pharmaceutical insertion composition of the present invention to be inserted in a single insertion the amount of from 3 to 10 g. For insertion into the urethra, the suitable amount is from 2 to 5 g. The pharmaceutical ingredient is thus contained in the composition in the amount that will provide the desired effect by a single insertion.

In the present invention, for applying the pharmaceutical ingredients which show a loss of medicinal effect by decomposition of the ingredient when preserved in the form of an aqueous solution for a long period, e.g., an antibiotic such as penicillin and others, or an adrenal cortical hormone, the pharmaceutical ingredient may be dissolved or admixed, at the time of the use, into or with a base composition for the pharmaceutical insertion composition of a given viscosity which has been obtained by dissolving a water-soluble base compound in an aqueous solution of carboxyvinyl polymer, and the composition may be inserted. Alternatively, the base composition may be previously mixed with propylene glycol. In this case, the pharmaceutical ingredient needs not be uniformly mixed with the base composition. When the required amount of pharmaceutical ingredient is inserted, the desired medicinal effect may be obtained.

When the pharmaceutical insertion composition of the present invention is inserted into the rectum, its concentration in the serum is as follows:

A pharmaceutical insertion composition obtained in Example 16 is inserted into the rectum of a rabbit having the body weight of 3.2 kg at the rate of 20 mg of 5-fluoroaracil per 1 kg of the body weight, and the concentration of 5-fluorouracil in the serum after the insertion is measured to show the following results:

| 45 minutes later | 0.33 μg/ml |
| 1 hour later | 0.31 μg/ml |
| 3 hours later | 0.086 μg/ml | since the 5-fluorouracil is known to have the effective concentration in blood at about 0.08 μg/ml, it has been known that it maintains sufficient effective concentration in blood even 3 hours after the insertion. When 5-fluorouracil is injected into vein, its concentration in blood already becomes less than the effective blood concentration 30 minutes later, and when used in the form of the conventional suppository or in the form of liquid, it is barely absorbed. Thus, it has been clearly known that the dosage in the form of the insertion composition of the present invention is quite excellent.

A pharmaceutical insertion composition obtained in Example 18 is inserted into the rectum of a beagle dog having the body weight of 10 kg at the rate of 300 mg of ibuprofen per dog, and the concentration of ibuprofen in the serum after the insertion is measured to show the following results:

| 1 | 1 hour later | 65 μg/ml |
| 2 | hours later | 53 μg/ml |
| 3 | hours later | 44 μg/ml |
| 4 | hours later | 40 μg/ml |
| 6 | hours later | 42 μg/ml |
| 8 | hours later | 35 μg/ml |
| 10 | hours later | 29 μg/ml |
| 12 | hours later | 15 μg/ml |

A pharmaceutical insertion composition obtained in Example 19 is inserted into the rectum of three rabbits having the body weight of 2.4–3.0 kg at the rate of 10 mg of indomethacin per 1 kg of the body weight, and the concentration of indomethacin in the serum after the insertion is measured to show the following results:

| 30 minutes later | 12 μg/ml |
| 60 minutes later | 8 μg/ml |
| 120 minutes later | 4.5 μg/ml |
| 240 minutes later | 2.5 μg/ml |
| 360 minutes later | 1 μg/ml |

Similarly, when carried by the composition of the present invention, other pharmaceutical ingredients are also favorably absorbed into the body without any undesirable side action, so that the pharmaceutical insertion composition of the present invention is suitable as a form of composition to be substituted for injection, internal dosage or conventional suppository. Especially, it is suitable as a base composition for effectively dosing the internals of such pharmaceuticals as a liable to induce stomach and intestines disturbance, pharmaceuticals to be decomposed in the stomach and intestines dosage as a substitute for the injections which have a danger of nerve disturbance, or pharmaceuticals which may give rise to a liver disturbance, or pharmaceuticals which are decomposed in the liver etc.

The present invention is illustrated by way of the following examples, but is not limited thereto. The viscosity is that measured by the C-type Viscosimeter made by Tokyo Keiki Co., Ltd., and unless specifically noted, is the value measured at 20° C.

EXAMPLE 1

Carboxyvinyl polymer (CARPOPOL 940) was dissolved in purified water to obtain 1% aqueous solution of carboxyvinyl polymer.

To 90 g of 1% aqueous solution of carboxyvinyl polymer were gradually added 6.075 g of 20% aqueous solution of triethanolamine, which were admixed with purified water to make the total volume 300 g, and sufficiently stirred to give a colorless, transparent gel of pH 7.0 and having viscosity of 30,500 centipoises. (Concentration of carboxyvinyl polymer was 0.3%)

In the similar manner to the above, gels were prepared by varying the concentrations of the carboxyvinyl polymer, and the viscosities of the gels thus obtained were as follows:

| Concentration of carboxyvinyl polymer (%) | Viscosity (centipoise) |
| --- | --- |
| 4.5 | 120,000 |
| 4.0 | 110,000 |
| 3.5 | 100,000 |
| 3.0 | 85,000 |
| 2.0 | 70,000 |
| 1.0 | 50,000 |
| 0.75 | 38,000 |
| 0.5 | 34,000 |
| 0.25 | 26,000 |
| 0.12 | 10,000 |

EXAMPLE 2

Carboxyvinyl polymer was dissolved in purified water to obtain 1.0% aqueous solution of carboxyvinyl polymer.

100 g of the above aqueous solution were neutralized with 6.75 g of aqueous solution of 20% triethanolamine and 4.36 g of purified water and evenly mixed to give a colorless, transparent gel. pH 7.0, concentration of carboxyvinyl polymer 0.9%.

In the similar manner, instead of triethanolamine, other water-soluble basic compound was added to neutralized the solution, and the concentration of the carboxyvinyl polymer was adjusted to 0.9% to give a gel, whose viscosity was measured to be, as follows:

| Water-soluble basic compound | Viscosity (centipoise) |
| --- | --- |
| Triethanolamine | 40,000 |
| Triethylamine | 37,500 |
| Aqueous ammonia | 38,500 |
| Sodium hydroxide | 38,500 |

EXAMPLE 3

To 37.5 g of 2% aqueous solution of carboxyvinyl polymer, 67.5 g of propylene glycol and 5.0625 g of aqueous solution of triethanolamine were added and neutralized. Then, to this mixture, 39.9375 g of purified water were added to obtain a colorless, transparent gel of 150 g in total volume. The concentration of carboxyvinyl polymer was 0.5%.

Instead of triethanolamine, other water-soluble basic compound was added to neutralize the gel. In the same manner as above, with the concentration of the carboxyvinyl polymer adjusted to 0.5%, the viscosity of the gel was measured to be, as follows:

| Water-soluble basic compound | Viscosity (centipoise) |
| --- | --- |
| Triethanolamine | 40,000 |
| Triethylamine | 45,000 |
| Aqueous ammonia | 40,000 |
| Sodium hydroxide | 34,000 |

EXAMPLE 4

100 g of 1% aqueous solution of carboxyvinyl polymer were neutralized with 180 g of polypropylene glycol and 6.75 g of aqueous solution of 20% triethanolamine, to which 113.25 g of purified water were added to obtain a colorless, transparent gel of 400 g in total volume. The concentration of carboxyvinyl polymer was 0.25%.

Instead of triethanolamine, other water-soluble basic compound was added to neutralize the gel. In the same manner as above, with the concentration of the carboxyvinyl polymer adjusted to 0.25%, the viscosity of the gel was measured to be, as follows:

| Water-soluble basic compound | Viscosity (centipoise) |
| --- | --- |
| Triethanolamine | 26,000 |
| Triethylamine | 25,000 |
| Aqueous ammonia | 22,500 |

EXAMPLE 5

10 g of sulpyrine were dissolved in 100 g of 2% aqueous solution of carboxyvinyl polymer, to which 13.5 g of 20% aqueous solution of triethanolamine were gradually added while stirring well. To the mixture, purified water was added to make the total volume 200 g, which was sufficiently stirred to give a colorless or pale yellow, transparent gel. Viscosity 12,500 centipoises.

EXAMPLE 6

7.5 g of sulpyrine were dissolved in 150 g of 3% aqueous solution of carboxyvinyl polymer, to which 30.375 g of 20% aqueous solution of triethylamine were gradually added while stirring. To the mixture, purified water was added to make the total volume 200 g, which was sufficiently stirred to give a colorless or pale yellow, transparent gel. Viscosity 68,000 centipoises.

EXAMPLE 7

10 g of aminopyrine were dissolved in 100 g of 2% aqueous solution of carboxyvinyl polymer, to which 13.5 g of 20% aqueous solution of triethanolamine were gradually added while stirring. To the mixture, purified water was added to make the total volume 200 g, which was sufficiently stirred to give a colorless, transparent gel. Viscosity 41,000 centipoises.

EXAMPLE 8

13.5 g of 20% aqueous solution of triethanolamine were gradually added to 100 g of 2% aqueous solution of carboxyvinyl polymer. The mixture was well stirred to make a gel, to which 10 g of sulpyrine and purified water were added to make the total volume 200 g, which was sufficiently stirred to give a colorless or pale yellow gel. Viscosity 12,500 centipoises.

EXAMPLE 9

2.5 g of predonisolone were suspended in 250 g of 2% aqueous solution of carboxyvinyl polymer, to which 33.7 g of 20% aqueous solution of triethanolamine were gradually added while stirring. To the mixture, purified water was added to make the total volume 500 g. A white, opaque gel was obtained. This was because the predonisolone was suspended in a state of fine crystalline powder without being dissolved. Viscosity 52,000 centipoises.

EXAMPLE 10

To 150 g of 2% aqueous solution of carboxyvinyl polymer, 200 g of propylene glycol solution, in which 1.0 g of predonisolone was dissolved, were added while stirring. To the mixture, 20.25 g of 20% aqueous solution of triethanolamine were gradually added, and purified water was added thereto to make the total volume 400 g. A colorless, transparent gel was obtained. Viscosity 68,000 centipoises.

EXAMPLE 11

20.25 g of 20% aqueous solution of triethanolamine were gradually added to 150 g of 2% aqueous solution of carboxyvinyl polymer, to which 200 g of propylene glycol solution, in which 1.0 g of predonisolone was dissolved, were added while stirring, and then, purified water was added thereto to make the total volume 400 g. A colorless, transparent gel was obtained. Viscosity 68,000 centipoises.

EXAMPLE 12

200 g of propylene glycol solution, in which 1.2 g of biosol were dissolved, were added to 150 g of 2% aqueous solution of carboxyvinyl polymer while stirring. To the mixture, 20.25 g of 20% aqueous solution of triethanolamine were added gradually, and then purified water was added to make the total volume 400 g. A colorless, transparent gel was obtained. Viscosity 62,000 centipoises.

EXAMPLE 13

To 150 g of 2% aqueous solution of carboxyvinyl polymer, 100 g of propylene glycol and 20.25 g of 20% aqueous solution of triethanolamine were gradually added. To the resulting mixture, 100 g of solution of propylene glycol, in which 1.2 g of biosol were dissolved, were added, and then, purified water was added thereto to make the total volume 400 g. A colorless, transparent gel was obtained. Viscosity 62,000 centipoises.

EXAMPLE 14

To 150 g of 2% aqueous solution of carboxyvinyl polymer, 200 g of propylene glycol, in which 2.0 g of ethyl aminobenzoate were dissolved, were added. To the resulting mixture 20.25 g of 20% aqueous solution of triethanolamine were gradually added while stirring, and purified water was added thereto to make the total volume 400 g to give a colorless, transparent gel. Viscosity 64,000 centipoises.

EXAMPLE 15

To 150 g of aqueous solution of carboxyvinyl polymer, 200 g of propylene glycol solution, in which 8.0 g of benzylalcohol were dissolved, were added. To the resulting mixture, 21.25 g of 20% aqueous solution of triethanolamine were gradually added while stirring, and purified water was added thereto to make the total volume 400 g to give a colorless, transparent gel. Viscosity 61,000 centipoises.

EXAMPLE 16

To 500 g of 2% aqueous solution of carboxyvinyl polymer, 135 g of 10% aqueous solution of triethanolamine were added while stirring to give 120 g of gel, to which 10 g of 5-fluorouracil and 30 g of trimethylolaminomethane were added gradually while stirring, and then, 40 g of purified water were added thereto to agitate well to give a colorless, transparent or slightly turbid gel. Viscosity 20,000 centipoises, 5-fluorouracil content 5%.

EXAMPLE 17

To 150 g of aqueous solution of carboxyvinyl polymer, 30.375 g of 20% aqueous solution of trimethylolaminomethane were added to give 136.76 g of gel, to which there were added 16.96 g of solution of trimethylolaminomethane in which 10 g of 5-fluorouracil were dissolved, and then, 36.3 g of purified water were added thereto to give a gel of 200 g in total volume, which was a colorless, transparent gel containing 5% of 5-fluorouracil having a viscosity of 39,500 centipoises (at 29° C.).

EXAMPLE 18

To 100 g of 4% aqueous solution of carboxyvinyl polymer, 16 g of 10% aqueous solution of sodium hydroxide were added while stirring to give a gel (pH 7). To 20 g of polyoxyethylene sorbitan monolaurate, 5 g of ibuprofen were dissolved by heating at about 80° C. To this mixture, the above obtained gel was added under heating at about 80° C. and stirring vigorously to make the total volume 100 g of gel. Viscosity 12,000 centipoises, pH 5.70, ibuprofen content 5%.

EXAMPLE 19

5 g of indomethacin and 0.5 g of polyethyleneglycol monolaurate were added to 83.5 g of purified water. To this mixture, a gel prepared by mixing 100 g of 4% aqueous solution of carboxyvinyl polymer and 16 g of 10% aqueous solution of sodium hydroxide, were added while stirring to make total volume 100 g of gel. Viscosity 12,000 centipoises, pH 6.65, indomethacin content 5%.

EXAMPLE 20

5 g of 5-fluorouracil and 15 g of trimethylolaminomethane were dissolved in 57.5 g of purified water while stirring and heating to about 80° C. on a water bath. To this solution, 22 g of 4% aqueous solution of carboxyvinyl polymer and 0.5 g of triethanolamine were added while stirring vigorously to make a gel. Viscosity 10,000 centipoises, pH 9.2, 5-fluorouracil content 5%.

EXAMPLE 21

5 g of 5-fluorouracil and 15 g of trimethylolaminomethane were dissolved in 49.8 g of purified water while stirring and heating to about 80° C. on a water bath. Then, to this solution, 29 g of 4% aqueous solution of carboxyvinyl polymer and 1.2 g of triethanolamine were added to make 100 g of gel. Viscosity 20,000 centipoises, pH 9.10, 5-fluorouracil content 5%.

EXAMPLE 22

5 g of 5-fluorouracil which were finely pulverized in a glass mortar, 1 g of polyoxyethylene sorbitan monolaurate, 1 g of sorbitan sesquioleate and 1 g of vitamin E acetate were mixed in 10 g of propylene glycol and the mixture was heated to about 80° C. To 43 g of gel prepared by mixing 100 g of 1% aqueous solution of carboxyvinyl polymer and 4 g of 10% aqueous solution of sodium hydroxide while stirring vigorously, 40 g of purified water were added while stirring and heating at about 80° C. To this solution, the above-mentioned mixture was added and stirred uniformly and cooled. Suspension gel preparation containing 5% of 5-fluorouracil was obtained. Viscosity 10,000 centipoises, pH 7.00.

EXAMPLE 23

1 g of 1-(2-tetrahydrofuryl)-5-fluorouracil was dissolved in 79 g of purified water by warming. To this solution, 20 g of gel which were prepared by mixing 100 g of 4% aqueous solution of carboxyvinyl polymer and 16 g of 10% aqueous solution of sodium hydroxide, were added to make a gel of 100 g. Viscosity 10,000 centipoises, pH 7.00.

EXAMPLE 24

5 g of flufenamic acid, 1 g of polyoxyethylene sorbitan monolaurate, 1 g of sorbitan sesquioleate, 2 g of vitamin E acetate and 0.2 g of dibucain were dissolved in 10 g of propylene glycol while heating to about 80° C. 38.8 g of purified water were mixed with 42 g of gel which were prepared by mixing 100 g of 1% aqueous solution of carboxyvinyl polymer and 4 g of 10% aqueous solution of sodium hydroxide, at about 80° C. To above gel, the above-mentioned propylene glycol solution was added to make 100 g of gel preparation container 5% of flufenamic acid. Viscosity 7,000 centipoises, pH 6.80.

EXAMPLE 25

6.5 g of mecreosol were dissolved in 250 ml purified water, and to this solution, 7.5 g of glycerin, 100 g of gel which were prepared by mixing 100 g of 4% aqueous solution of carboxyvinyl polymer and 16 g of 10% aqueous solution of sodium hydroxide, and 142.5 g of purified water were added and stirred vigorously to make a gel. To 50 g of this gel, 92.6 mg of insulin (27.0 international units/mg) were added and stirred. A suspension gel preparation having 50 international units/ml of insulin was obtained. Viscosity 20,000 centipoises, pH 7.00.

What is claimed is:

1. A method of administering a pharmaceutical composition to the human body comprising inserting into the rectum, vagina or urethra a pharmaceutical insertion composition consisting essentially of a mixture of:
   (a) 0.1 to 5.0% by weight of a carboxyvinyl polymer in the form of an aqueous solution;
   (b) A water-soluble basic compound for neutralizing said carboxyvinyl polymer to adjust the preparation to a pH value of 4 to 10, said water-soluble basic compound selected from the group consisting of an alkylamine, a dialkylamine, an alkanolamine, a dialkanolamine, a trialkanolamine, trimethylolaminomethane, ammonia and an alkali metal hydroxide, wherein said alkyl and alkanol each have 1 to 6 carbon atoms;

(c) a pharmaceutically effective amount of a pharmaceutical ingredient selected from the group consisting of insulin and an anti-inflammatory and analgesic compound selected from ibuprofen, ketoprofen, flurbiprofen and dichlofenac sodium;

said composition being a gel having a pH value of from 4 to 10 and a viscosity of from 5,000 to 100,000 centipoises at 20° C., whereby the pharmaceutical ingredient is absorbed through the rectal, vaginal or urethral tissue into the blood stream of the human body.

2. A method according to claim 1, wherein the pharmaceutical ingredient is insulin and the pharmaceutical insertion composition is applied to the rectal or vaginal tissue.

3. A method according to claim 1, wherein the pharmaceutical ingredient is ibuprofen, ketoprofen or flurbiprofen and the pharmaceutical insertion composition is applied to the rectal tissue.

* * * * *